(12) United States Patent
Paladini et al.

(10) Patent No.: US 6,702,749 B2
(45) Date of Patent: *Mar. 9, 2004

(54) OPTICAL NEEDLE GUIDE FOR ULTRASOUND GUIDED NEEDLE BIOPSY

(75) Inventors: Gianluca Paladini, Princeton, NJ (US); Frank Sauer, Princeton, NJ (US)

(73) Assignee: Siemens Corporate Research, Inc., Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/202,352

(22) Filed: Jul. 24, 2002

(65) Prior Publication Data

US 2003/0028112 A1 Feb. 6, 2003

Related U.S. Application Data

(60) Provisional application No. 60/307,520, filed on Jul. 24, 2001.

(51) Int. Cl.⁷ .................................................. A61B 8/14
(52) U.S. Cl. .................... 600/464; 600/461; 600/437; 606/130; 601/2
(58) Field of Search .................... 600/407–472; 606/130; 601/2

(56) References Cited

U.S. PATENT DOCUMENTS

| | | | | |
|---|---|---|---|---|
| 4,484,569 A | * | 11/1984 | Driller et al. | 600/439 |
| 4,527,569 A | * | 7/1985 | Kolb | 600/461 |
| 4,651,732 A | * | 3/1987 | Frederick | 606/130 |
| 4,763,662 A | * | 8/1988 | Yokoi | 600/461 |
| 4,932,414 A | * | 6/1990 | Coleman et al. | 600/445 |
| 5,056,917 A | * | 10/1991 | Nowacki et al. | 356/124 |
| 5,316,014 A | * | 5/1994 | Livingston | 600/567 |
| 5,647,373 A | * | 7/1997 | Paltieli | 600/567 |
| 5,810,841 A | * | 9/1998 | McNeirney et al. | 606/130 |
| 6,030,348 A | * | 2/2000 | Unger et al. | 600/564 |
| 6,096,049 A | * | 8/2000 | McNeirney et al. | 606/130 |
| 6,110,112 A | * | 8/2000 | Heywang-Koebrunner | 600/461 |
| 6,146,390 A | * | 11/2000 | Heilbrun et al. | 606/130 |
| 6,206,890 B1 | * | 3/2001 | Truwit | 606/130 |
| 6,216,029 B1 | * | 4/2001 | Paltieli | 600/427 |
| 2003/0120154 A1 | * | 6/2003 | Sauer et al. | 600/459 |

* cited by examiner

*Primary Examiner*—Dennis W. Ruhl
*Assistant Examiner*—William C Jung

(57) ABSTRACT

An optical guide for a biopsy needle includes a light projector for producing a line image on a patient's skin surface, wherein the light projector is adapted for mounting on an ultrasound transducer such that the line image corresponds with an intersection of the transducer ultrasound plane with the skin surface.

21 Claims, 6 Drawing Sheets

OPTICAL NEEDLE GUIDE FOR ULTRASOUND GUIDED NEEDLE BIOPSY

Figure 1A:
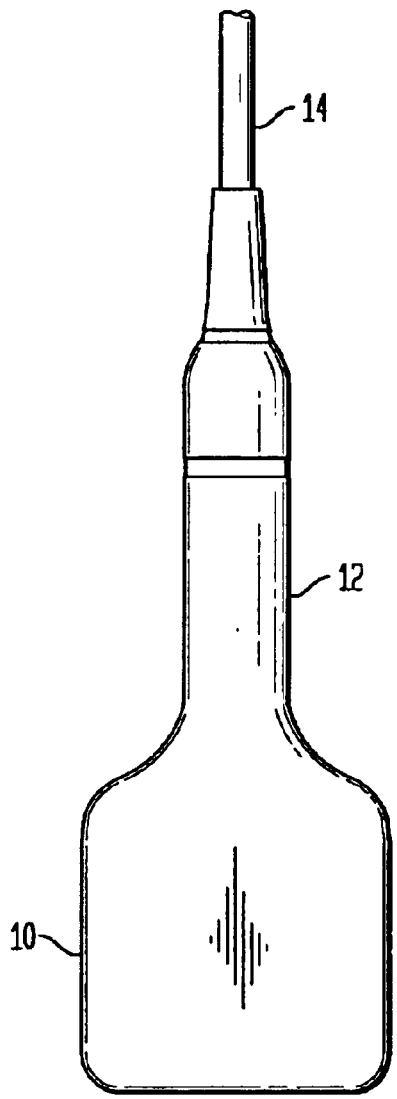
Figure 1B:
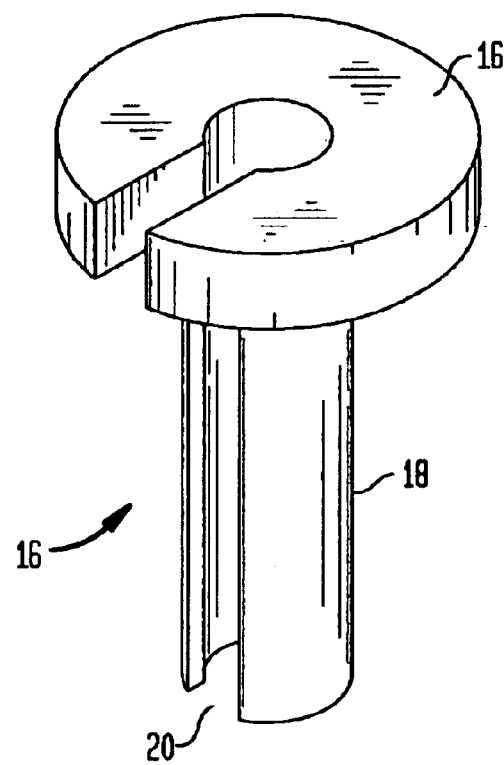
Figure 1C:
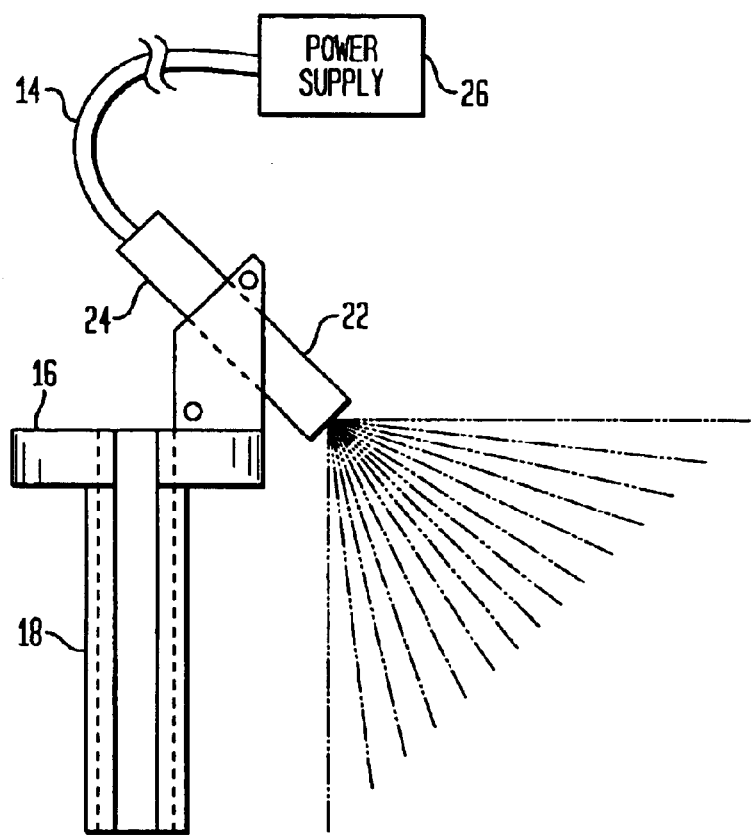
Figure 1D:
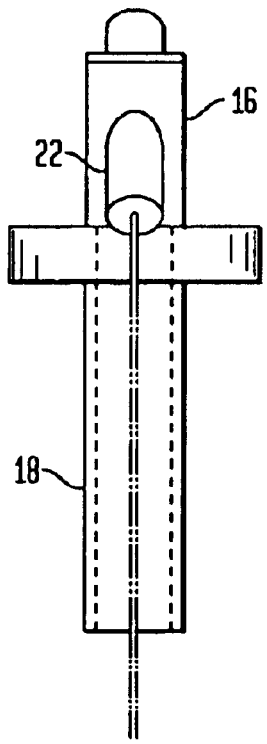

Reference is hereby made to copending U.S. Provisional Application No. 60/307,520, filed Jul. 24, 2001 in the name of the present inventors, whereof the disclosure is herein incorporated by reference and whereof the benefit is claimed.

The present invention relates to the field of medical biopsy and, more particularly, to needle biopsy.

For a typical needle biopsy, a biopsy needle has to be inserted into an anatomical target to remove a tissue sample. Ultrasound guidance using ultrasound imaging is routinely used as, for example, for breast needle biopsy. The real-time ultrasound images allow the operating physician to locate the target and to monitor the needle position. The ultrasound imaging apparatus is well-known and descriptions can be found in articles, texts, and the trade literature.

Generally the procedure is performed "in-plane". With the ultrasound transducer being in a position where the target is visible in the image, the insertion point of the needle is chosen on the intersection of the ultrasound plane and the patient's skin surface. The needle is oriented so that it lies in this plane and points towards the target. When the needle is now inserted, it will appear in the ultrasound image, and its progress along its path towards the target can be monitored.

It is herein recognized that one difficulty with performing an ultrasound guided needle biopsy in this manner is to correctly position and orient the needle to be in the same plane with the ultrasound image. Mechanical needle guides are commercially available to facilitate this task. They are clipped onto the transducer and constrain the movement of the needle so that it is forced to stay in a plane aligned with the transducer. Even though the needle can now reliably be placed in the plane of the ultrasound image, many physicians find the rigid constraint imposed by the use of this mechanical guide too inflexible and consequently do not use it. They want to be able to make corrective adjustments to the path of the needle as it approaches the target, which is not easily possible with the constraints of the mechanical needle guide. Because the mechanical guide constrains the needle entry point to be close to the transducer, it is then also not possible to insert the needle at some distance from the transducer, which is desirable for shallow needle angles.

An object of the present invention is to utilized an optical needle guide to facilitate in-plane needle alignment while preserving the full flexibility of a free-hand procedure.

In accordance with another aspect of the present invention, an optical guide for a biopsy needle comprises mounting apparatus for affixing a light projector onto an ultrasound imaging device; and the light projector including projection components for producing a line image on a patient's skin such that the line image coincides with an imaging plane of the ultrasound device.

In accordance with another aspect of the present invention, an optical guide for a biopsy needle comprises a light projector for producing a line image on a patient's skin surface; the light projector being adapted for mounting on an ultrasound transducer exhibiting an ultrasound plane, such that the line image corresponds with an intersection of the ultrasound plane with the skin surface.

In accordance with another aspect of the present invention, an optical guide for a biopsy needle comprises a light projector for producing a line image on a patient's skin surface; the light projector being adapted for mounting on an ultrasound transducer exhibiting an ultrasound imaging plane; and the light projector being aligned such that the line image corresponds with an intersection of the ultrasound imaging plane with the skin surface so as to indicate a line of insertion for the biopsy needle located in the ultrasound imaging plane.

In accordance with another aspect of the present invention, an optical guide for a biopsy needle comprises apparatus for affixing a light projector onto an ultrasound imaging device; and the light projector including apparatus for producing a line image on a patient's skin such that the line image coincides with an imaging plane of the ultrasound device.

In accordance with another aspect of the present invention, an optical guide for a biopsy needle comprises light projector apparatus; the light projector apparatus being incorporated in an ultrasound imaging device; and the light projector apparatus including projection components for producing a line image on a patient's skin such that the line image coincides with an imaging plane of the ultrasound device.

In accordance with another aspect of the present invention, an optical guide for a biopsy needle as recited in claim 32, wherein at least a portion of the light projector apparatus is integrally formed with the ultrasound imaging device.

In accordance with another aspect of the present invention, an optical guide for a biopsy needle comprises a light projector for producing a line image on a patient's skin surface; the light projector being incorporated into an ultrasound transducer exhibiting an ultrasound plane, such that the line image corresponds with an intersection of the ultrasound plane with the skin surface.

In accordance with another aspect of the present invention, a method for optically guiding a biopsy needle comprises the steps of: affixing a light projector for producing a line image on a patient's skin onto an ultrasound imaging device, such that the line image coincides with an imaging plane of the ultrasound device; ultrasound imaging the patient for a desired biopsy target; and selecting a point in relation to the line image for inserting the biopsy needle appropriately for the target.

In accordance with another aspect of the present invention, a method for optically guiding a biopsy needle comprising the steps of: incorporating a light projector for producing a line image on a patient's skin into an ultrasound imaging device, such that the line image coincides with an imaging plane of the ultrasound device; ultrasound imaging the patient for a desired biopsy target; and selecting a point in relation to the line image for inserting the biopsy needle appropriately for the target.

In accordance with another aspect of the present invention, an optical guide for a biopsy needle includes a light projector for producing a line image on a patient's skin surface, wherein the light projector is adapted for mounting on an ultrasound transducer such that the line image corresponds with an intersection of the transducer ultrasound plane with the skin surface.

Figure 2:
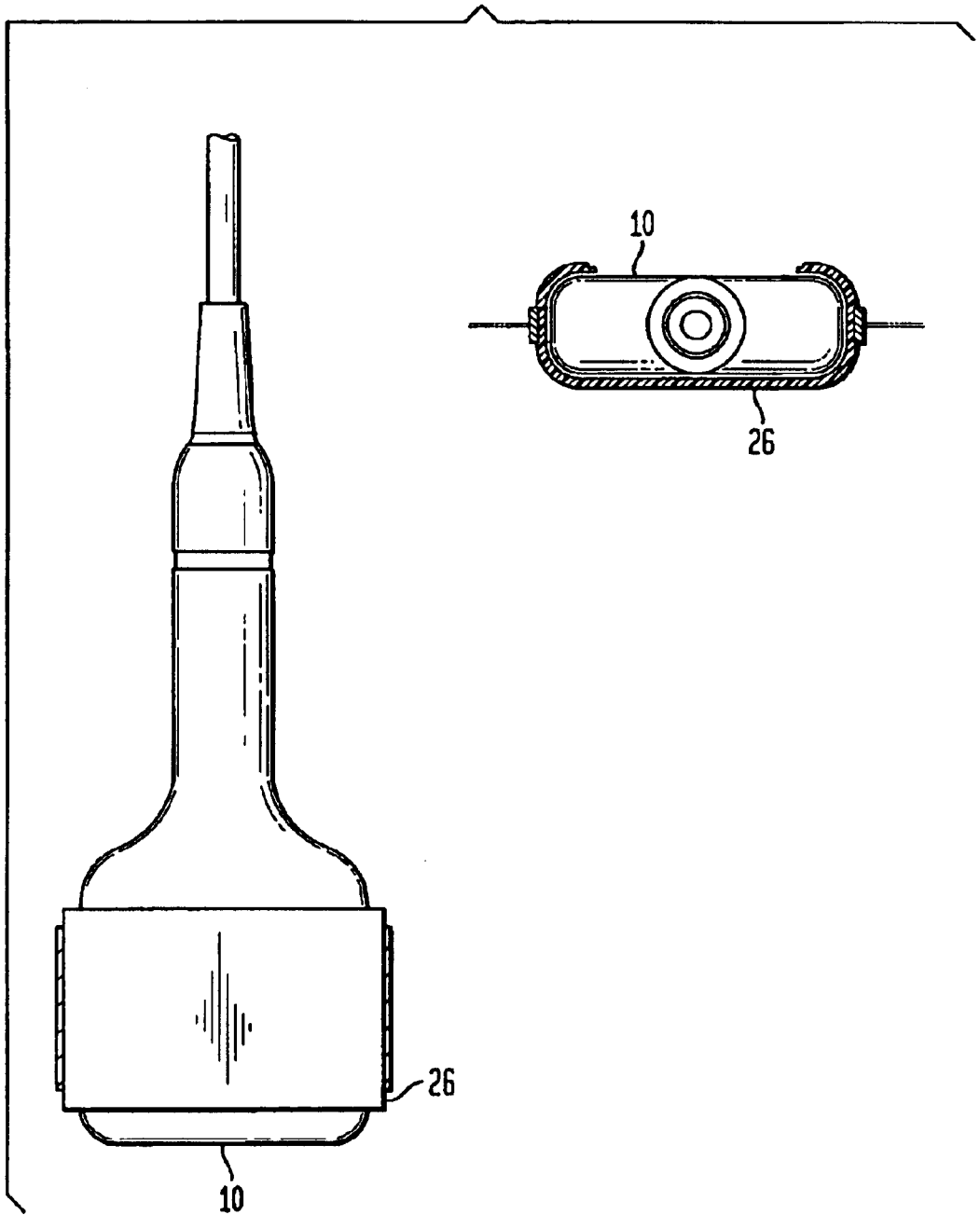

The invention will be better understood from the detailed description of preferred embodiments which follows, in conjunction with the various figures of the Drawing, in which FIGS. 1 and 2 show in diagrammatic form embodiments in accordance with the principles of the invention;

FIGS. 3–6 show photographs of an embodiment of the invention using Edmund Scientific laser diode module L54-177 with single line projection head L54-185; and FIGS. 7–10 show in diagrammatic form, various embodiments of the invention.

Figure 5:
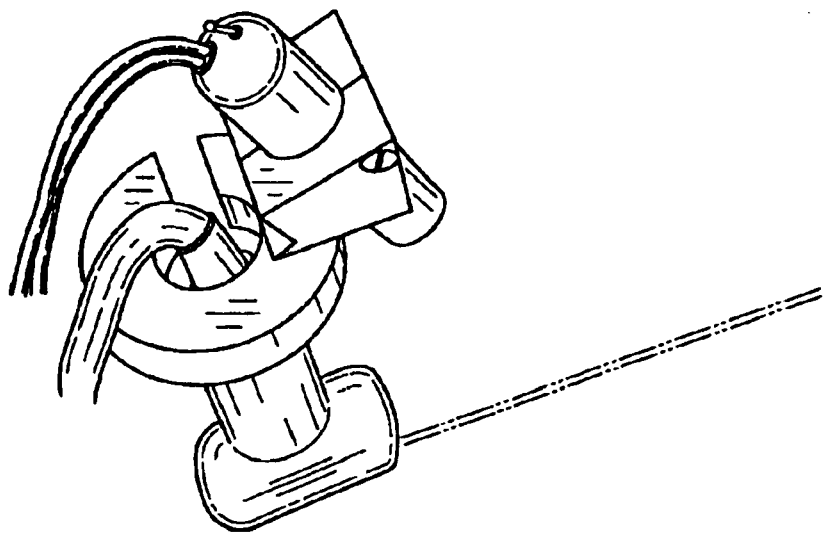
Figure 6:
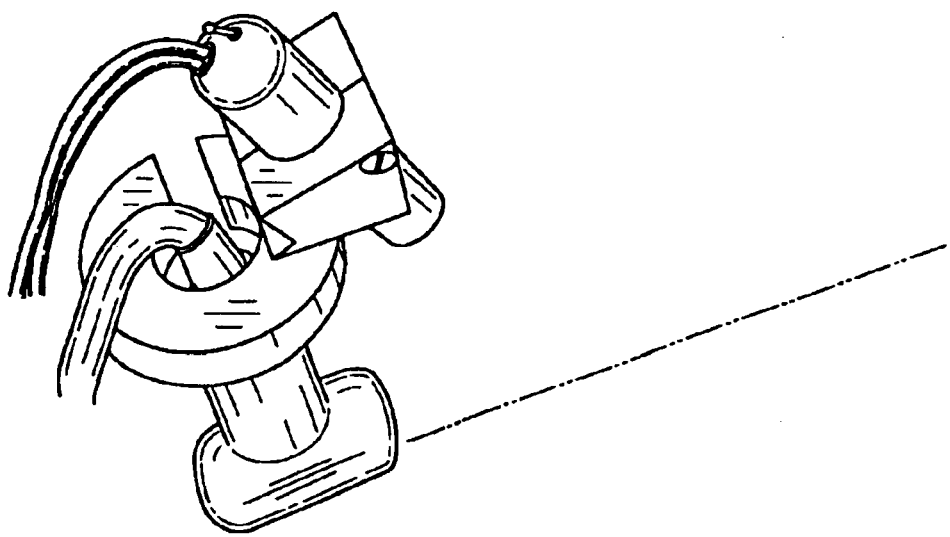

In accordance with another aspect of the present invention, a light source 22, such as a laser source, is attached to the transducer 10 by way of a laser mount and emits a planar beam of light so as to project a line of light onto the skin surface, as shown in FIGS. 5 and 6. Light source 22 received power from a power supply 26. The planar beam of light is coplanar with the plane of the ultrasound image that is being captured by the transducer. Hence, the line of light on the patient's skin marks the intersection of the ultrasound plane with the patient's skin surface and thereby marks the possible in-plane entry points for the needle. The user places the tip of the needle on the line of light on the skin, and can then also adjust an in-plane orientation of the needle guided by the light projection. In such an in-plane pose, the needle is seen illuminated along its length.

FIG. 1 shows a preferred embodiment in accordance with the present invention.

An ultrasound transducer 10, having a handle 12, is coupled conventionally by a cable 14 for interaction with ultrasound apparatus, not shown, for providing an ultrasound image to an operator, typically a physician. A mounting unit 16 in accordance with the principles of the invention comprises a platform portion 16 connected to a cylindrical portion 18. Mounting unit 16 may be an integrally formed unitary piece or it may be fabricated by joining separate parts forming platform portion 16 and cylindrical portion 18. Cylindrical portion 18 exhibits a slot 10 sufficiently wide to allow passage of cable 14 so that mounting unit 16 can be mounted onto transducer 10 by slipping cylindrical portion 18 over handle 12. Being essentially in the form of a hollow cylinder adapted to fit over the handle of the ultrasound transducer unit, mounting unit 16 may be made of any convenient and suitable material, such as metal or plastic.

In an experimental set-up, a small laser unit with line optics was utilized, using by way of example, an Edmund Scientific laser diode module L54-177 with single line projection head L54-185. By adjustment and design choices, mounting unit 16 enables the optical axis of laser in the plane of the ultrasound transducer imaging plane. The adjustment is easily performed by turning the laser around its optical axis in mechanical mount 16 do as to align the projected line of laser light with the plane of the ultrasound transducer.

For convenience in operation, one arrangement is for mechanical mount 16 to be located above the operator's hand. However, mounting below the operator's hand position is also practicable using a clip-on type of mount 26, as is commonly used for the mechanical guides heretofore mentioned. See FIG. 2, which shows side and top views utilizing such an arrangement, wherein like reference numerals indicate corresponding parts in the apparatus.

It is herein recognized that that the foregoing embodiments showing the laser unit being mounted as an accessory to the ultrasound transducer have the additional advantage of easy retrofitting to many ultrasound transducers already in use in the medical field Nevertheless, it is also desirable to incorporate the optical guide into the ultrasound transducer, preferably by integrally forming the two in one molding. An alternative is to attach the units together by glue or fasteners. While the separate component embodiments are not heavy to handle, a well-designed unitary construction can be even lighter. This also makes it easier to incorporate the supply wires in the same cable and connector assembly, making for a neater arrangement.

On the other hand, it is also noted that a further benefit of the separate attachable unit is that its introduction into service need not await a decision to redesign existing ultrasound units for an integral embodiment and experience can be first gained in operational use with ultrasound transducers of varying designs, before committing to tooling up for production of an integral version.

FIGS. 3, 4, 5, and 6 show different aspects of embodiments of the invention, using Edmund Scientific laser diode module L54-177 with single line projection head L54-185.

Figure 3:
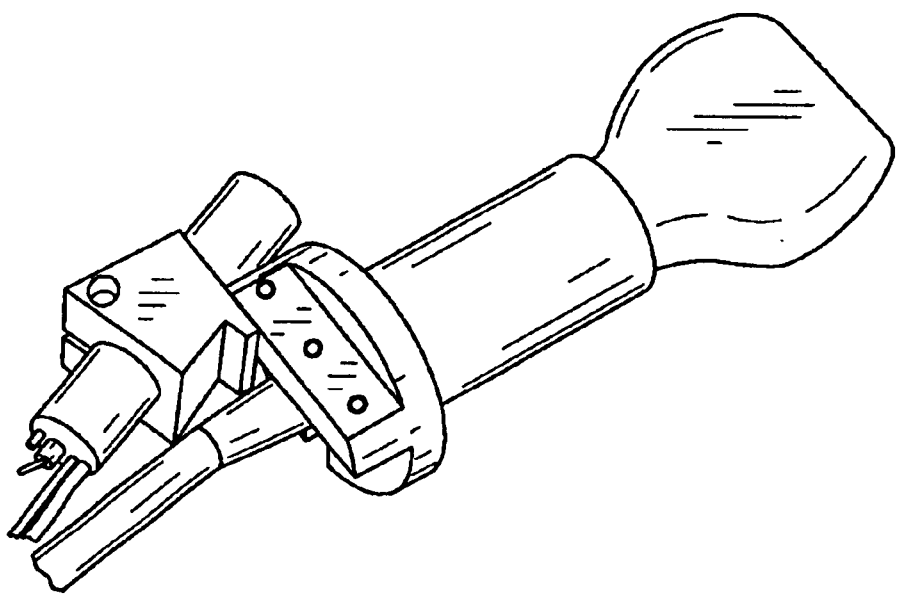
Figure 4:
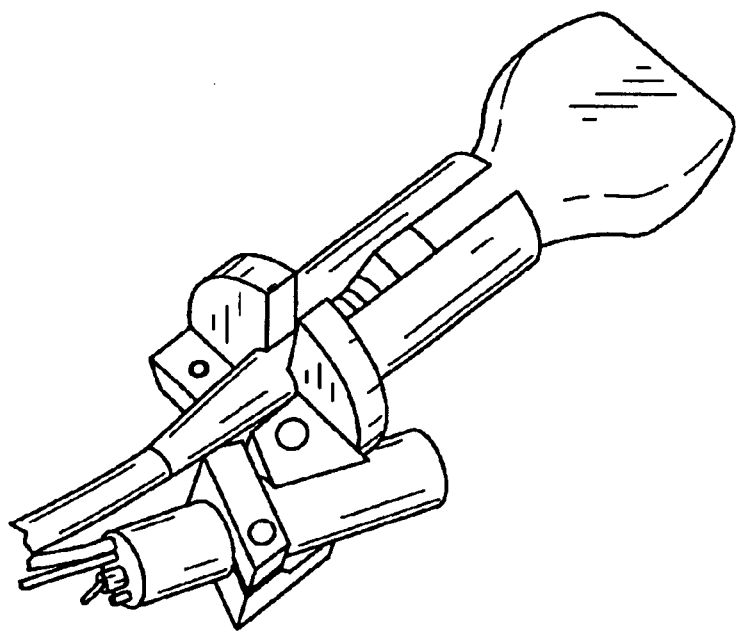

More particularly, FIG. 3 shows a frontal view and FIG. 4 a back view of the embodiment of the invention using Edmund Scientific laser diode module L54-177 with single line projection head L54-185. FIG. 5 show the apparatus in operation, with the picture taken with the laser in sharp focus and FIG. 6 shows the same with the projected line in sharp focus.

In place of the laser utilized in the present illustrative it is also practicable to use any of a number of optical arrangements to establish the light line on the patient's skin. For example, microoptics can be employed; diffractive or holographic optics may be utilized instead of refractive optics or catoptrical arrangements may be used as known in the arts of optical image projection. Generally, good depth of focus is desirable.

It is further contemplated that the required optical projection can be obtained by the use of a scanning device rather than the line optic devices described above. Scanners are known, such as a flying-spot scanner.

Alternative light sources may be utilized, such as light emitting diodes (LED's) or an array of LED's. For another example, an external light source coupled by optical fiber for light transmission with line projection optics provides for a small, compact, and light weight embodiment, herein recognized to be desirable in the application of the present invention. Handedness considerations for right- or left-handed users are also readily accommodated by providing for appropriate mounting or by a two sided illuminator.

Figure 7:
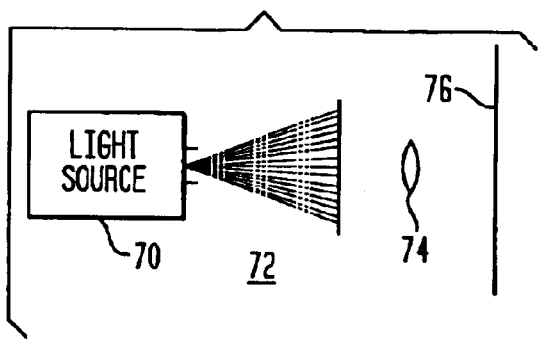

FIG. 7 shows in diagrammatic form an embodiment in accordance with the present invention wherein a light source 70 with a fiber optic assembly 72 with a projection lens 74 for producing a line image on a projection surface 76.

Figure 8:
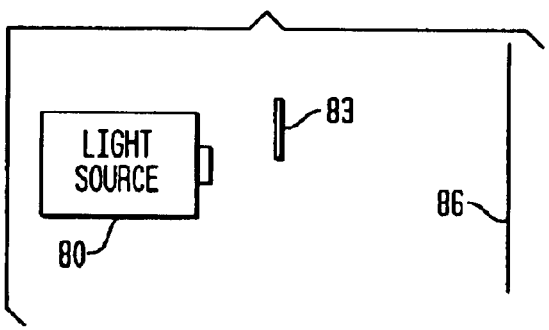

FIG. 8 shows in diagrammatic form an embodiment in accordance with the present invention wherein a light source 80 with a holographic plate 83 for producing a line image in conjunction with light from source 80 on a projection surface 86.

Figure 9:
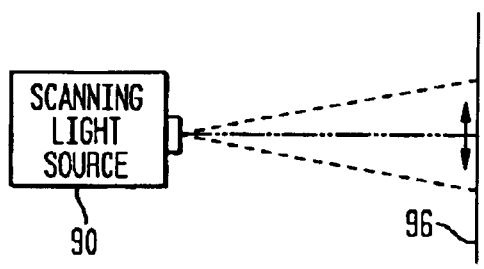

FIG. 9 shows in diagrammatic form an embodiment in accordance with the present invention wherein a light source 90 with a scanning, sweeping, or oscillating source of light for producing a line image on a projection surface 96. The image scan rate is selected to avoid flicker, or alternatively, to produce a rate of flicker that can be helpful to identifying the line more readily.

Figure 10:
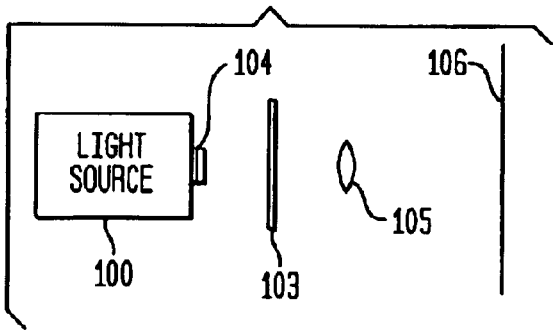

FIG. 10 shows in diagrammatic form an embodiment in accordance with the present invention wherein a light source 100 with a slide projection plate 103 with a condenser 104 and a projection lens 105 for producing a line image on a projection surface 106.

The various modifications shown with particular embodiments may be incorporated in different combinations. For example, a flicker rate that may be desirable can readily be incorporated with LED's and a choice of different colors can be provided with the fiber optic arrangement or, for example, with the slide arrangement in FIG. 10.

These and the like changes will be apparent to one of skill in the art of the invention. It is contemplated that such variations and substitutions are within the spirit of the present invention which is defined by the claims following.

What is claimed is:

1. An optical guide for a biopsy needle comprising:
   a light projector for producing a line of light on a patient's skin surface;
   said light projector mounted on an ultrasound transducer exhibiting an ultrasound imaging plane; and
   said light projector being aligned such that said line of light corresponds with an intersection of said ultrasound imaging plane with said skin surface so as to indicate a line of potential entry points for said biopsy needle located in said ultrasound imaging plane.

2. An optical guide for a biopsy needle in accordance with claim 1, wherein said light projector is mounted by cooperative engagement with said ultrasound transducer.

3. An optical guide for a biopsy needle in accordance with claim 1, wherein said light projector is mounted on said ultrasound transducer by way of a sliding sleeve arrangement fitting over a corresponding handle of said transducer.

4. An optical guide for a biopsy needle in accordance with claim 2, wherein sliding sleeve arrangement comprises a slot for facilitating passage of a supply cable to said transducer.

5. An optical guide for a biopsy needle in accordance with claim 1, wherein light projector utilizes a laser projector.

6. An optical guide for a biopsy needle in accordance with claim 1, wherein light projector utilizes a light emitting diode.

7. An optical guide for a biopsy needle in accordance with claim 1, wherein light projector utilizes a light emitting diode array.

8. An optical guide for a biopsy needle in accordance with claim 1, wherein light projector utilizes a laser projector in conjunction with line optics.

9. An optical guide for a biopsy needle in accordance with claim 1, wherein light projector utilizes a laser projector in conjunction with fiber optics.

10. An optical guide for a biopsy needle in accordance with claim 1, wherein light projector utilizes holographic projection.

11. An optical guide for a biopsy needle in accordance with claim 1, wherein light projector utilizes a scanning projector.

12. An optical guide for a biopsy needle in accordance with claim 11, wherein said scanning projector is a flying spot scanner.

13. An optical guide for a biopsy needle in accordance with claim 11, wherein said scanning projector utilizes a mechanically operated scan.

14. An optical guide for a biopsy needle in accordance with claim 1, wherein light projector utilizes slide projection.

15. An optical guide for a biopsy needle in accordance with claim 1, wherein light projector includes means for selecting one of a plurality of colors for said line of light.

16. An optical guide for a biopsy needle comprising:
    a light projector for producing a line of light on a patient's skin surface;
    said light projector incorporated into an ultrasound transducer exhibiting an ultrasound plane, such that said line of light corresponds with an intersection of said ultrasound plane with said skin surface.

17. An optical guide for a biopsy needle as recited in claim 16, wherein at least a portion of said light projector is integrally formed with said ultrasound imaging device.

18. A method for optically guiding a biopsy needle comprising the steps of:
    affixing a light projector for producing a line of light on a patient's skin onto an ultrasound imaging device, such that said line of light coincides with an imaging plane of said ultrasound device;
    ultrasound imaging said patient for a desired biopsy target; and
    selecting a point from one of a plurality of potential entry points along the line of light for inserting said biopsy needle in a path toward said target.

19. A method for optically guiding a biopsy needle in accordance with claim 18 wherein said step of selecting a point further comprises the step of:
    aligning the biopsy needle with the line of light such that the biopsy needle is illuminated along its length by the light projector.

20. A method for optically guiding a biopsy needle comprising the steps of:
    incorporating a light projector for producing a line of light on a patient's skin into an ultrasound imaging device, such that said line of light coincides with an imaging plane of said ultrasound device;
    ultrasound imaging said patient for a desired biopsy target; and
    selecting a point from one of a plurality of potential entry points along the line of light for inserting said biopsy needle in a path toward said target.

21. A method for optically guiding a biopsy needle in accordance with claim 20 wherein said step of selecting a point further comprises the step of:
    aligning the biopsy needle with the line of light such that the biopsy needle is illuminated along its length by the light projector.

* * * * *